United States Patent [19]

Monte et al.

[11] 3,953,295

[45] Apr. 27, 1976

[54] REAGENT FORMULATIONS FOR GLUCOSE ASSAY

[75] Inventors: Alexander A. Monte; Ching Chiang, both of Glendora, Calif.

[73] Assignee: Mallinckrodt, Inc., St. Louis, Mo.

[22] Filed: May 6, 1974

[21] Appl. No.: 467,423

Related U.S. Application Data

[60] Division of Ser. No. 200,552, Nov. 19, 1971, Pat. No. 3,816,262, which is a continuation-in-part of Ser. No. 190,883, Oct. 20, 1971, abandoned.

[52] U.S. Cl............................ 195/103.5 R; 195/63; 195/68; 195/99; 195/103.5 C
[51] Int. Cl.²........................................ G01N 31/14
[58] Field of Search................ 195/63, 68, 103.5 R, 195/103.5 C, 100, 99

[56] References Cited
UNITED STATES PATENTS

| | | | |
|---|---|---|---|
| 3,321,019 | 2/1968 | Hammer et al. | 195/63 X |
| 3,413,198 | 11/1968 | Deutsch | 195/63 X |
| 3,627,688 | 12/1971 | McCarty et al. | 195/63 X |
| 3,858,854 | 1/1975 | Won et al. | 195/68 X |

*Primary Examiner*—David M. Naff
*Attorney, Agent, or Firm*—Mathew D. Madsen

[57] ABSTRACT

Glucose is assayed in biological specimens using granular, water soluble, substantially anhydrous, storage-stable reagent formulations containing enzymes, a chromogen and/or a buffer and a nitrogen - containing polyoxyalkylene nonionic surfactant obtained by the sequential reaction of ethylenediamine with propylene oxide and ethylene oxide in the presence of a catalyst. The surfactant contains polyoxypropylene chains having an average molecular weight of between about 750 and about 6,750, and polyoxyethylene chains constituting between about 10 and about 80 weight percent. The surfactant has an advantageous effect on granulation, dissolution and storage stability of the reagent formulations and is effective for solubilizing protein such as enzymes.

14 Claims, 1 Drawing Figure

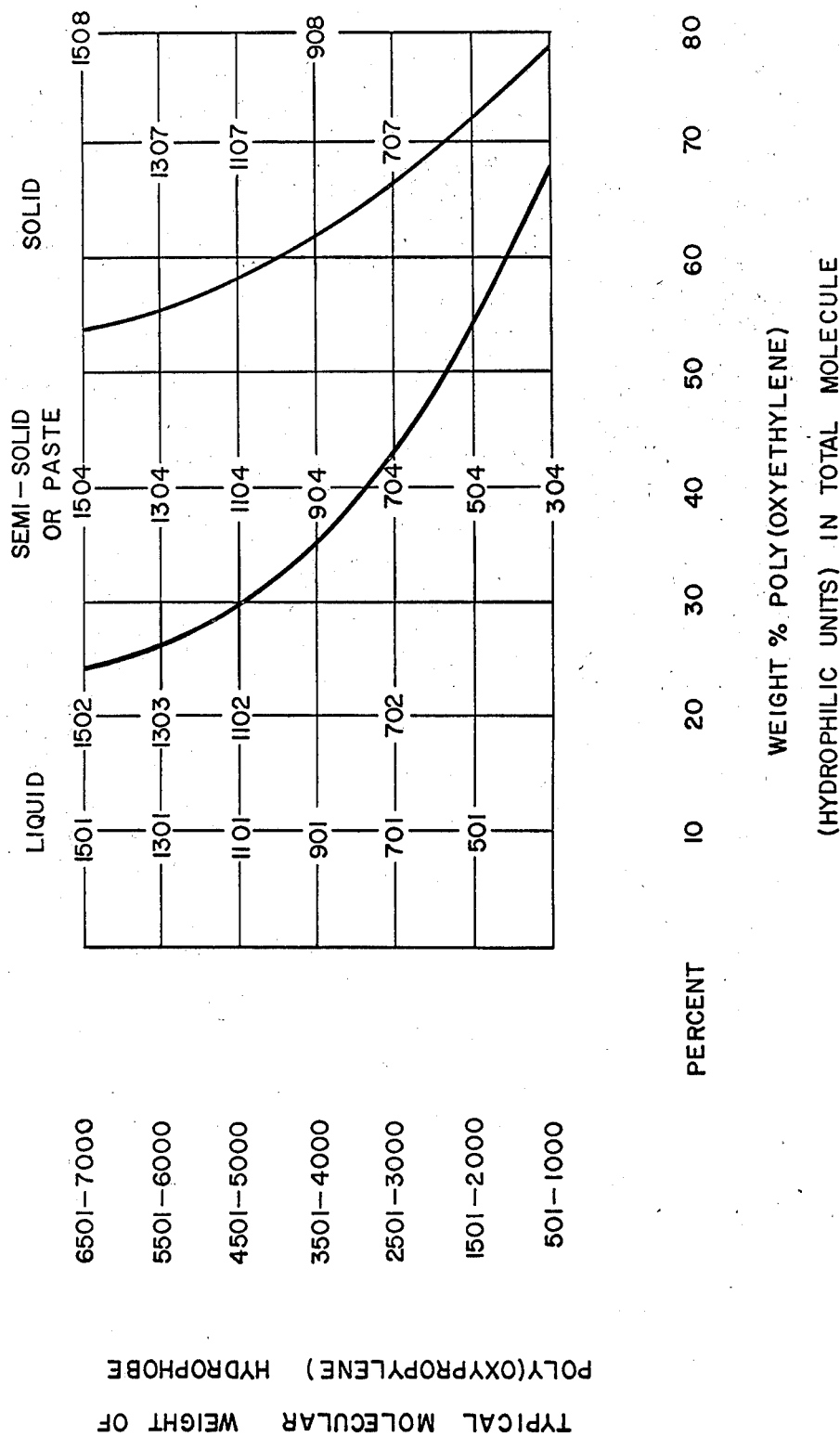

3,953,295

REAGENT FORMULATIONS FOR GLUCOSE ASSAY

CROSS-REFERENCE TO RELATED APPLICATION

This application is a division of our copending, coassigned U.S. Pat. application Ser. No. 200,552, filed Nov. 19, 1971, now U.S. Pat. No. 3,816,262, which is a continuation-in-part of our U.S. Pat. application Ser. No. 190,883, filed Oct. 20, 1971, now abandoned.

BACKGROUND OF THE INVENTION

This invention relates to the field of clinical diagnostic testing and more particularly to novel reagents and methods for making biological assays on body fluids.

A large variety of test reagents and methods are available for use in determining the character of various body fluids to assist in the diagnosis of certain pathological conditions. Tests for determination of certain types of biological activity or the presence and quantity of certain biologically active components provide information indicating the presence or absence of disease or other physiological disorder. In accordance with such tests, the biological specimen to be analyzed, for example, a sample of a body fluid, is typically mixed with a liquid reagent formulation which contains a reagent capable of effecting a reaction which causes a measurable change in the specimen/reagent system. Very often the reaction which takes place in the test is an enzymatic reaction. Certain tests are designed, in fact, to determine the presence of a particular enzyme and in such cases the reagent formulation may contain a substrate upon which the enzyme to be determined is known to act. In other cases, the determination may be for a material which is known to be a reactive substrate in an enzymatically catalyzed reaction. In either case, the reagent formulation very commonly contains an enzyme, a coenzyme or both. Because the catalytic activity of most enzymes is specific to a particular reaction, test reagents can be formulated which are effective to determine specific biological components or activities even in a complex body fluid containing a large number of other components which might interfere with efforts to obtain a purely chemical analysis. Moreover, many of the components which are to be determined have highly complex chemical structures which would render direct chemical analysis difficult even in the absence of any contaminants.

Unfortunately, enzymes and coenzymes are generally rather delicate materials which may be readily denatured by heating and which also tend to degenerate upon storage. Many of the substrate materials used in biological assay reagent formulations are similarly unstable. Liquid reagents containing such components are therefore not generally susceptible to storage and must be freshly prepared shortly prior to use in clinical diagnostic testing. Because of the relative expense of enzymes and coenzymes and the skill required to prepare a reagent formulation containing these materials which can be utilized to obtain accurate clinical diagnostic test results, the instability of the liquid formulations has motivated a substantial amount of research to develop reagents in a relatively storage-stable form. Much of this effort has been directed to the development of solid, dry, water-soluble formulations which can be dissolved in water at the time of testing to provide a fresh liquid reagent useful in the test. Typical prior art dry reagent formulations are disclosed in Deutsch U.S. Pat. No. 3,413,198 and Stern et al. U.S. Pat. No. 3,546,131.

A dry reagent formulation satisfactory for use in preparing liquid reagents for routine clinical diagnostic tests should satisfy a number of criteria. It must be readily soluble in a solvent compatible with the biological specimen, usually water. It should be capable of solubilizing proteinaceous material in the specimen. Moreover, it should be readily susceptible to packaging in convenient sized packages and be adapted for rapid dissolution in the solvent to provide a liquid reagent of proper strength for a given test or series of tests.

SUMMARY OF THE INVENTION

It is an object of the present invention to provide improved dry, water-soluble, reagent formulations for use in conducting clinical diagnostic tests. It is a further object of the present invention to provide such formulations which can be readily granulated and shipped or stored in granular form. It is a particular object of the invention to provide such reagent formulations in free-flowing, granular form at consistent bulk densities so that they may be delivered to a volumetric packaging or tableting operation in consistent weight amounts. Additional objects of the invention include the provision of dry reagent formulations having a high capacity for solubilizing protein; the provision of such formulations having a high degree of storage stability; the provision of methods for preparing the dry reagent formulations of the invention; and the provision of methods for conducting clinical diagnostic tests utilizing such reagent formulations. Other objects and features will be in part apparent and in part pointed out hereinafter.

In one of its aspects, therefore, the present invention is directed to a reagent formulation for use in conducting a clinical diagnostic test on a biological specimen. The reagent formulation comprises a solid, water-soluble, substantially anhydrous, storage-stable mixture containing a reagent capable of participating in a test reaction to effect a measurable change in a test system, and a solid nitrogen-containing polyoxyalkylene nonionic surfactant. The surfactant has a structure corresponding to that obtained when ethylene diamine is reacted sequentially with propylene oxide and ethylene oxide in the presence of a catalyst and the polyoxypropylene chains of the surfactant have an average molecular weight of between about 750 and about 6750.

The invention is further directed to a method of conducting a clinical diagnostic test on a biological specimen using the aforementioned reagent formulation. The method comprises dissolving the reagent formulation in water to produce a liquid reagent; mixing the liquid reagent with a specimen to form a specimen/reagent test system; and measuring a change in the system resulting from the reaction between the reagent and the specimen.

The invention is also directed to a method of preparing the novel reagent formulation. The method comprises the steps of mixing a reagent capable of participating in a test reaction to effect a measurable change in a test system, a nitrogen-containing polyoxyalkylene nonionic surfactant of the above-noted character, and a solvent for the surfactant; and removing the solvent to form a substantially anhydrous, water-soluble, free-flowing, granular solid.

DESCRIPTION OF THE DRAWING

The DRAWING is a grid illustrating the molecular structure of various commercially available nonionic surfactants useful in the practice of the invention. The coordinates of each point on the grid correspond to the chain size of the polyoxyethylene hydrophile and polyoxypropylene hydrophobe moieties of a particular surfactant. Boundary lines set out on the grid separate the areas encompassing surfactants which assume different physical states.

DESCRIPTION OF THE PREFERRED EMBODIMENTS

To facilitate preparation of liquid reagents from solid formulations in the clinical laboratory, it is highly desirable to package the solid formulations in proper unitary amounts. Thus, for example, the solid formulations may be encapsulated or tabletted with the proper quantity of reagent in each capsule or tablet for conducting a single test. Alternatively, a multi-test package can be provided from which the proper amount of liquid reagent is prepared for conducting a specified number of tests.

Where a solid reagent formulation is packaged in unitary amounts, accuracy of metering the solid material into each capsule, tablet or multi-test package is important. The metering equipment which is used for delivering solid materials in packaging and tableting operations, however, almost universally operates on a volumetric basis. Unless the solid material is free-flowing and has a consistent bulk density, therefore, it cannot be delivered in consistent weight amounts to each package, capsule or tableting station using conventional equipment.

To provide a solid formulation in free-flowing form of consistent bulk density, it is preferably granulated prior to packaging. Granulation converts a powdered material into a material constituted by small agglomerates of relatively uniform size. Properly prepared, the granular material is free-flowing, has a consistent bulk density and is readily handled by the metering devices used in packaging operations. To granulate a powdered material, the powder is typically mixed with a binder dissolved in a volatile solvent, wet screened, dried by driving off the solvent, and dry screened following the drying step. In addition to the binder, a lubricating substance is normally incorporated in the granulation mass to further enhance the flow characteristics of the granules, especially under the compressive stress of tableting operations.

As noted, solid formulations useful as reagents for conducting clinical diagnostic tests on biological specimens should have certain additional properties. Because they are dissolved in water to produce a liquid reagent, all components, including the binder, should be readily water-soluble. Because many of the tests involve enzymatic reactions and/or proteinaceous substrates, the formulation should possess detergent properties for solubilizing protein.

It has now been discovered that the above objectives can be met and that effective clinical reagent formulations for the determination of certain biological properties of body fluids can be produced in free-flowing, granular form through the use of particular nitrogen-bearing polyoxyalkylene nonionic surfactants. Test formulations granulated with the aid of these surfactants are well adapted to precision packaging and tableting operations. Because of their free-flowing character and consistent bulk density, they can be delivered to either a packaging or tableting operation in consistent weight amounts by volumetric metering. As a consequence, clinical test reagents formulated at a central location remote from a clinical laboratory can be utilized to prepare liquid test reagents for clinical use without the need for weighing, analyzing, or other procedures by the clinical chemist or technician.

The nitrogen-containing surfactants which are useful in the formulations of the invention possess the unique multiple capability of serving as binders, lubricants and solubilizers for protein. Moreover, they are themselves water-soluble, thus promoting the dissolution of the reagent fromulations in water to provide clinical liquid reagents. These surfactants are sold under the trade designation "Tetronic" by Wyandotte Chemical Corporation. They are normally prepared by sequential reaction of first propylene oxide and then ethylene oxide with ethylene diamine in the presence of an alkaline or acid catalyst. Normally these surfactants are prepared at elevated temperatures using alkaline catalysts such as sodium hydroxide, potassium hydroxide, sodium alkoxide, quarternary ammonium bases and the like. Other methods are available for the preparation of these surfactants. The preparation of surfactants such as those utilized in the formulations of the invention is more fully described in U.S. Pat. 2,979,528.

The properties and physical state of nonionic surfactants having structures corresponding to those derived from ethylene diamine, propylene oxide and ethylene oxide vary with the lengths of the polyoxypropylene and polyoxyethylene chains. As the drawing shows, the physical state of these surfactants is largely dependent upon the proportionate weight of the surfactant constituted by the polyoxyethylene chains, but is also influenced by the average molecular weight of the polyoxypropylene moieties. The polyoxypropylene chains are hydrophobic while the polyoxyethylene chains are hydrophilic. Thus, the surfactants having polyoxypropylene units of low average molecular weight are more water-soluble than those having polyoxypropylene units of a higher average molecular weight. The numbers set out on the face of the grid correspond to particular members of the Tetronic series. Each number is located at a point on the grid whose coordinates correspond to the polyoxyethylene and polyoxypropylene chain sizes of the particular product which is commercially designated by said number.

Essentially any surfactant whose structure is defined by the coordinants of a point lying in the grid of the drawing may be utilized in the formulations of the invention. It is preferred, however, that the surfactant be solid or at least semi-solid. A greater proportion of the solid surfactants can be satisfactorily incorporated in a reagent formulation and thus a greater binding and lubricating capacity is obtained without adversely affecting other properties of the formulation. Desirably, on the order of 2.5 to 5% by weight of the preferred solid surfactants are incorporated in the reagent formulations. When the liquid formulations are used, it is not always possible to incorporate more than 2 or 3% by weight of the surfactant without imparting a somewhat waxy character to the formulation. The use of 2 to 3% by weight of a liquid "Tetronic" surfactant produces a useful product, but the binding and lubricating capabilities of the surfactant are not always fully exploited at such a level. Granules having the most desirable properties are obtained using solid or semi-solid surfactants.

Since the dry reagent formulations of the invention are dissolved in water for use in conducting clinical diagnostic tests, it is also desirable that the surfactant component promote the dissolution of the granular product. Thus, it is preferred that the surfactant be as hydrophilic as possible, i.e., that the molecular weight of the polyoxypropylene hydrophobe moiety of the surfactant be relatively low. Thus, the preferred surfactants for use in the formulations of the invention are those which are both solid or semi-solid in physical state and relatively hydrophilic. Solid-state surfactants with polyoxypropylene chains having an average molecular weight of loss than about 4,000 are especially preferred, with the most suitable surfactants being those whose polyoxypropylene chains have an average molecular weight of between about 2,750 and about 3,750 and whose weight percentage of polyoxyethylene units is between about 70% and about 80%. Two particular surfactants whose weight and structure characteristics fall within the latter limits are those sold under the trade designations Tetronic 707 and Tetronic 908. Tetronic 707 has a polyoxypropylene hydrophobe molecular weight on the order of 2,750 and a weight percentage of polyoxyethylene units of about 70% while Tetronic 908 has a polyoxypropylene molecular weight of about 3,750 and a weight percentage of polyoxyethylene units of about 80%. Good results are also obtained with surfactants whose polyoxypropylene chains have an average molecular weight of between 750 and 4,000 with a weight percentage of between about 35% and about 65% polyoxyethylene units. Other surfactants within the grid of the drawing are reasonably satisfactory but less effective than those represented by the right lower corner of the grid.

In addition to their advantageous effect upon granulation and dissolution of dry clinical test reagent formulations, surfactants of the abovenoted character have been found to be effective for solubilizing protein. As indicated above, this is a highly advantageous characteristic, since enzymes and other proteinaceous matter derived from either the reagent formulation or the specimen commonly participate in the test reactions. By solubilizing protein, the surfactants function to facilitate the progress of the test reaction and thus enhance the effectiveness of the reagent formulation. It may, therefore, be seen that incorporation of these surfactants in clinical test formulations uniquely provides multiple advantages in the preparation, packaging, dissolution and functional operation of clinical reagent formulations.

It has further been discovered that the dry clinical reagent formulations of the invention are quite stable and generally possess good shelf life characteristics. Although we cannot precisely account for the particular ingredient or combination of ingredients which imparts the high degree of storage stability, it appears that such stability may be a somewhat general characteristic of dry clinical reagent formulations which include the particular nitrogen-containing nonionic surfactants used in our formulations. If so, the ability to impart storage-stability represents a further aspect of the unique multiple function of this type of surfactant in such formulations.

To prepare the reagent formulations of the invention, the surfactant is mixed with a volatile solvent and at least one reagent capable of participating in a test reaction to effect a measurable change in a reagent/specimen test system. The surfactant should be soluble up to the amount present in the solvent which is utilized. Solvents which may be used include methylene chloride, chloroform, methanol, benzene, water, methanol/water, and chloroform/methylene chloride. After through mixing and appropriate size classification, the solvent is removed to yield a granular product.

In a preferred embodiment of the invention, the ingredients of the formulation, in dry particulate form, are thoroughly blended in a mechanical mixer. With the mixer running, a granulating solution containing the solvent and the surfactant, preferably that sold under the trade designation Tetronic 707 or Tetronic 908, is added. Additional solvent is used as needed to produce granular agglomerates of the desired size and wetness.

The resulting wet granulation is screened through a coarse screen, for example 10 mesh, then spread in thin layers in trays and dried at reduced pressure, for example, 25 Hg absolute or less. Depending on the heat sensitivity of the formulation, drying is normally carried out at room temperature or at modest elevated temperature (up to about 37°C.). Generally, the depth of the wet granules in the trays should not exceed about one-half inch to three-fourths inch.

After completion of the drying cycle, the dried granulation is rescreened through a finer screen, for example, 20 to 30 mesh, blended thoroughly and packaged in containers essentially impervious to moisture. Since the components of the reagent formulation are frequently moisture sensitive, the formulation should not be exposed to a relative humidity of more than about 5% after removal from the dryer.

The reagent formulations of the invention are adapted to be packaged in small unitary packages. For example, sufficient reagent formulation for a single assay may be tabletted or packaged in a capsule. The reagent formulations are also adapted to packaging in such containers as foil strip packets, utilizing automatic packaging machinery. Utilizing this packaging approach, sufficient reagent formulation to carry out a suitable predetermined number of tests, such as 10, 25, or 50 tests, may be accurately packaged in a single foil packet. The user then simply dissolves the contents of the multiple test packet in a predetermined volume of water and uses a suitable aliquot of the resulting liquid reagent in the performance of each of a series of assays for the desired biological substance or property.

In some instances, depending on the nature of the components and their compatibility, all of the reagents necessary in a single assay or determination may be included in a single formulation. In other instances, incompatibilities and/or other considerations may make it desirable to segregate certan reagents in which case two or more reagent formulations are prepared in accordance with the invention.

To conduct a clinical diagnostic test using the formulations of the invention, the liquid reagent produced by dissolving the dry formulation in a predetermined amount of water is mixed with the biological specimen in a predetermined volumetric or weight ratio. With the aid of appropriate instrumentation as required, the resulting specimen/reagent system is observed for the presence, absence, nature and extent of a physical, chemical or biological change. Such change as does occur is measured to provide the desired information for use in the clinical diagnosis.

Exemplary reagent formulations prepared in accordance with the invention and useful for the determination of hemoglobin, blood urea nitrogen, total protein, serum glutamic oxaloacetic transaminase, alkaline phosphatase, glucose, inorganic phosphorus, lactate dehydrogenase-L, serum glutamic pyruvic transaminase, uric acid (colorimetric) and uric acid (u.v.) are set forth in Table 1. The preferred compositions of these reagent formulations and methods for preparing them are described in the examples following Table 1 which more fully illustrate the invention.

anhydrous reagent formulation, sufficient for 50,000 tests, was obtained.

Upon being stored at a temperature of 45°C., the above-prepared formulation was found to be stable for at least 23 weeks which is equivalent to a stability period of 92 weeks at room temperature.

Dissolve in water, formulation A yields a liquid reagent useful in assaying blood hemoglobin. By action of the dissolved reagent, erythocytes in the blood are hemolyzed releasing hemoglobin which is oxidized to methemoglobin. Methemoglobin is converted to cyan- Table 1

Exemplary Clinical Test Reagent Formulations

| Formulation | Type of Formulation | Dry Ingredients (Reagents, Etc.) Name/Formula | Wt. (g.) | Granulating Solution | | | Theoretical Yield (g.) | No. of Tests (Thousands) |
|---|---|---|---|---|---|---|---|---|
| | | | | TETRONIC 707 (g.) | Polyethylene glycol 6000 (g.) | $CH_2Cl_2$ (ml.)[1] | | |
| A | Reagent Formulation for Hemoglobin Assay | $NaHCO_3$<br>$K_3Fe(CN)_6$<br>KCN<br>Mannitol | 300<br>50<br>30<br>590 | 30 | | (a) 200<br>(b) 300 | 1000 | 50 |
| K | Chromogen Formulation for Glucose Assay | o-Dianisidine·2HCl<br>Mannitol | 7.5<br>423.6 | 14.4 | 4.5 | (a) 150<br>(b) 125 | | 30 |
| L | Buffer Formulation for Glucose Assay | $NaH_2PO_4 \cdot H_2O$<br>$Na_2HPO_4$<br>Mannitol<br>Spray Dried Gum Arabic | 311.4<br>190.8<br>52.8<br>30.0 | 15.0 | | (a) 40[2]<br>(b) 5–10[2] | 600 | 30 |
| M | Enzyme Formulation for Glucose Assay | Glucose Oxidase Stabilized<br>Mannitol<br>Horseradish Peroxidase<br>Mannitol | 420<br>30 | 15.0 | 3.0 | (a) 40[2]<br>(b) 10[2] | 450 | 30 |

[1] (a) indicates amount of $CH_2Cl_2$ used as carrier for Tetronic 707.
(b) indicates amount of additional $CH_2Cl_2$ used to optimize granulation.
[2] Solvent is water instead of $CH_2Cl_2$.

EXAMPLE 1

Hemoglobin Reagent Formulation and Assay

Composition of the reagent formulation useful for hemoglobin assay is set forth as formulation A in Table 1.

To prepare this formulation, sodium bicarbonate (300 g.), milled potassium ferricyanide (50 g.) and potassium cyanide (30 g.) were initially added to a Hobart bowl and mixed with a stainless steel spatula. Mannitol (590 g.) was then added and the resulting blend was agitated for five minutes in the mixer. While agitation was continued, a solution of Tetronic 707 (30 g.) in methylene chloride (200 ml.) was added. An additional amount of methylene chloride (300 ml.) was then added to produce the proper granulation.

The wet granulation was screened through a No. 10 mesh stainless steel screen and the wet screened material was transferred to 8 × 12 inches Pyrex drying trays, at a depth of between about one-half inch and about three-fourths inch in each tray. The granulation was then dried in a vacuum oven for 15 hours at a temperature of 35°C. and a pressure of 25 inches Hg.

The dried granulation was removed from the vacuum oven in an environment where the relative humidity was not more than 5%. The dried granulation was then screened through a No. 20 mesh stainless steel screen using an Erweka oscillator. The screened, dried granulation was transferred to a P.K. blender and mixed for 5 minutes, then packaged in tightly closed containers. Approximately 1000 g. of a water-soluble, substantially methemoglobin whose formation alters the optical density of the reagent/specimen system. The optical density of the reagent/speciment system is measured at 540 nm. using a suitable spectrophotometer and compared against a reagent blank set at 100% transmission. The hemoglobin level is then determined by reference to a standard curve.

To prepare a liquid reagent sufficient for 50 tests, formulation A (1.00 g.) is dissolved in distilled water and the resulting solution is diluted to 250 ml. and mixed thoroughly. The reagent solution thus produced is stable for three months at room temperature if protected from light.

To conduct the hemoglobin assay test, a reagent/specimen test system is prepared by adding 20 microliters of well mixed blood (collected with an anticoagulant) to 5 ml. of the above solution of formulations A in a clean test tube. The contents of the tube are mixed thoroughly and allowed to stand at room temperature for at least 5 minutes. The optical density is then measured as described above to determine the hemoglobin level.

EXAMPLE 2

Glucose Reagent Formulations and Assay

For the glucose test, three separate formulations are provided. These are set forth in Table 1 as formulations K, L and M. Predetermined amounts of these formulations are dissolved in separate portions of water to provide liquid reagents for use in making the glucose assay.

To prepare chromogenic reagent formulation K, mannitol (423.6 g.) and o-dianisidine dihydrochloride (3,3-dimethoxybenzidine dihydrochloride) (7.5 g.) were blended in a Hobart bowl and agitated to promote intimate mixing. With the mixer running, a solution of "Tetronic 707 (14.4 g.) and polyethylene glycol-6,000 (4.5 g.) in methylene chloride (150 ml.) was introduced. Additional methylene chloride (125 ml.) was subsequently added to produce the desired degree of granulation and wetness. The wet granulation was screened and dried at room temperature, and the resultant dry granulation rescreened and packaged in the manner described in Example 1 for hemoglobin reagent formulation A.

Buffer reagent formulation L was prepared by blending monobasic sodium phosphate (311.4 g.), dibasic sodium phosphate (190.8 g.), mannitol (52.8 g.) and spray dried gum arabic (30.0 g.) in a Hobart bowl and agitating the resulting blend to promote intimate mixing. With the mixer running, a solution of Tetronic 707 (15.0 g.) in distilled water (40 ml.) was introduced. Additional distilled water (10 ml.) was subsequently added to produce the desired degree of granulation and wetness. The wet granulation was screened and dried and the resultant dry granulation rescreened and packaged in the manner described in Example 1 for hemoglobin reagent formulation A.

To prepare modified glucose oxidase, gum arabic (60 g.) and mannitol (40 g.) were dissolved in water (about 1,600 ml.) and the resulting colloidal solution was titrated to pH 7.0 with 2% sodium hydroxide. After titration, the solution was diluted to 2 liters with distilled water and clarified by centrifugation at 10,000 rpm with a No. 872 angle rotor in an IEC B-20 refrigerated centrifuge. The clear supernatant inert solution was collected and stored at 4°C. Bovine serum albumin (2 g.) was dissolved in 200 ml. of the aboveprepared inert solution with the aid of a magnetic stirrer. Liquid glucose oxidase (200 ml.) having a specific activity greater than 1,000 titrimetric units per ml. was then slowly added and the resulting mixture stirred for an additional 5 minutes to insure good mixing. This solution was transferred into freeze drying vessels, each vessel being filled with 150–200 ml. of the solution. The solution was frozen in thin layers by rotating the vessels in a dry ice/alcohol bath at −60°C. or below. The frozen layers were lyophilized for 16 to 20 hours at −60°C. to −70°C. and an absolute pressure of 5mµ Hg. The resultant lyophilized powder was collected under an atmosphere having a relative humidity of less than 5% and stored in a dessicator at 4°C. Approximately 14 g. of dry lyophilized glucose oxidase powder with a specific activity range of 14–16 IU/mg. at 37°C. was obtained.

In the preparation of enzyme reagent formulation M, a glucose oxidase (GOD) subformulation was initially produced. The above modified glucose oxidase (sufficient to provide 45 units of unmodified material/test) and mannitol (sufficient to provide 14 mg. — total of modified GOD plus mannitol - per test) were blended in a Hobart bowl and thoroughly agitated to promote intimate mixing. With the mixer running, a solution of Tetronic 707 (15.0 g.) and polyethylene glycol-6,000 (3.0 g.) in distilled water (40 ml.) was introduced. Additional distilled water (10 ml.) was subsequently added to produce the desired degree of granulation and wetness. The wet granulation was screened and dried at room temperature, and the resultant dry granulation rescreened in the manner described in Example 1 for hemoglobin reagent formulation A. The dry, rescreened granulated glucose oxidase subformulation was transferred to a tared 1,500 cc amber bottle and stored in a dry room pending subsequent intermixture with the other constituents of formulation M, as described below. Each gram of this granulated glucose oxidase subformulation contains sufficient GOD for the conduct of 71 glucose tests. The yield of this formulation in terms of potential tests units may therefore be calculated as follows:

No. of tests = wt. of GOD subformulation (g.) × 71 tests/g.

A peroxidase trituration subformulation for formulation M was prepared by blending, with mortar and pestle, an amount of horseradish peroxidase (POD) and an amount of mannitol sufficient for the number of tests calculated above and determined by the following respective calculations:

$$POD(mg.) = No.\ of\ tests \times \frac{440\ units}{test} \times \frac{1}{K\ (units/mg.)}$$

$$mannitol\ (g.) = \left[ No.\ tests \times \frac{1.0\ mg.}{test} - \frac{mg.\ POD}{test} \right]$$

$$\times \frac{1\ g.}{1000\ mg.}\ K\ \frac{units\ POD}{mg.\ POD}$$

being determined by prior assay.

To the trituration thus provided, 25 g. of the glucose oxidase subformulation was added and the resultant mixture agitated with a stainless steel spatula to disperse the trituration.

After preparation of the GOD/POD dispersion 50 g. of the GOD subformulation, the dispersion, and an additional 50 g. of the GOD subformulation, were sequentially screened through a 40 mesh stainless steel screen onto a clean receiving surface. All of the screened material was then transferred to a PK blender, along with the remainder of the GOD subformulation, and mixed for more than 5 minutes. The resultant blended granulation was transferred into 8 × 12 inch Pyrex trays at a depth of one-half to three-fourths inch and dried for about 15 hours at room temperature and a total pressure of 25 inches Hg.

Dissolved in two separate portions of water, formulation K, and formulation L together with M, provide liquid reagent solutions useful in the determination of true glucose in a biological specimen such as blood serum. In the presence of water and the glucose oxidase component of enzyme formulation M, glucose in the specimen is oxidized to gluconic acid with hydrogen peroxide formed as a by product. The by product, hydrogen peroxide, oxidizes the o-dianisidine constituent of chromogenic reagent formulation K, in the presence of horseradish peroxidase, producing a colored product which causes an increase in optical density at 445 nm. The extent of the increase indicates the concentration of glucose in the test system.

A chromogenic liquid reagent is prepared by dissolving formulation K (0.75 g.) in 50 ml. water. A liquid reagent having both enzyme activity and buffering capacity is prepared by dissolving formulation M (0.75 g.) and formulation L (1.0 g.) in another 50 ml. portion of distilled water. The chromogenic liquid reagent should be prepared fresh daily. The liquid reagent containing formulations L and M is stable for at least 1 week if refrigerated. The resulting solutions are sufficient for conducting 50 tests.

In the conduct of the test, 1 ml. each of the solution of formulation K and the solution containing formulations L and M are added to a clean, dry test tube. 10 microliters of serum are added to the tube and the resultant mixture is blended thoroughly and incubated at 37°C. for exactly 15 minutes. The optical density of the test system is then read at 445 nm against a reagent blank set at 100% transmission and the proportion of true glucose in the specimen determined from a standard curve.

Glucose standard curves are linear up to 300 mg% using the formulations and assay procedure of this example. Sera with high glucose levels (<300 Mg%) should be diluted with saline (0.9% NaCl) before analysis and the calculation corrected with the dilution factor.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. An enzyme reagent formulation for use in assaying a biological specimen for glucose comprising a granular, water-soluble, substantially anhydrous, storage-stable mixture containing glucose oxidase, peroxidase, gum arabic, mannitol, bovine serum albumin and a nitrogen-containing polyoxyalkylene nonionic surfactant obtained by the sequential reaction of ethylenediamine with propylene oxide and ethylene oxide in the presence of a catalyst, said surfactant containing polyoxypropylene chains having an average molecular weight of between about 750 and about 6,750 and polyoxyethylene chains constituting between about 10 and about 80 weight percent of said surfactant.

2. A reagent formulation as set forth in claim 1 wherein the nitrogen-containing polyoxyalkylene nonionic surfactant is solid and the polyoxypropylene chains thereof have an average molecular weight of less than abou 4,000.

3. A reagent formulation as set forth in clam 2 wherein the polyoxypropylene chains of the nitrogen-containing polyoxyalkylene nonionic surfactant have an average molecular weight of about 2,750 and the weight percentage of the polyoxyethylene units thereof is about 70%.

4. A method of preparing a granular, water-soluble, substantially anhydrous, storage-stable enzyme reagent formulation for use in assaying a biological specimen for glucose which comprises preparing a mixture of glucose oxidase, gum arabic, mannitol, bovine serum albumin, a solid nitrogen-containing polyoxyalkylene nonionic surfactant obtained by the sequential reaction of ethylene diamine with propylene oxide and ethylene oxide in the presence of a catalyst, said surfactant containing polyoxypropylene chains having an average molecular weight of between about 750 and 6,750, and polyoxyethylene chains constituting between about 10 and about 80 weight percent of said surfactant, and a solvent for the surfactant; and removing the solvent to form a substantially anhydrous, free-flowing, water-soluble, granular solid.

5. A method as set forth in claim 4 wherein the nitrogen-containing polyoxyalkylene nonionic surfactant is solid and the polyoxypropylene chains thereof have an average molecular weight of less than about 4,000.

6. A method as set forth in claim 5 wherein the polyoxypropylene chains of the nitrogen-containing polyoxyalkylene nonionic surfactant have an average molecular weight of about 2,750 and the weight percentage of the polyoxyethylene units thereof is about 70%.

7. A method as set forth in claim 6 wherein the mixture is screened in wet form prior to the removal of the solvent.

8. The method as set forth in claim 7 wherein the formulation is again screened after the solvent is removed.

9. A method as set forth in claim 8 wherein the solvent is removed by drying under reduced pressure.

10. A method of preparing a granular water-soluble, free-flowing, substantially anhydrous, storage-stable enzyme reagent formulation for use in assaying a biological specimen for glucose which comprises: (1) preparing a first mixture containing: glucose oxidase, gum arabic, mannitol, bovine serum albumin, a nitrogen-containing polyoxyalkylene nonionic surfactant obtained by the sequential reaction of ethylene diamine with propylene oxide and ethylene oxide in the presence of a catalyst, the surfactant containing polyoxypropylene chains having an average molecular weight of between about 750 and 6,750, and polyoxyethylene chains constituting between about 10 and about 80 weight percent of the surfactant, and a solvent for the surfactant; (2) removing the solvent to form a substantially anhydrous, free-flowing, water-soluble, granular first subformulation; (3) preparing a second mixture containing peroxidase and mannitol, the second mixture constituting a second subformulation; and (4) blending the first and second subformulations to provide a substantially anhydrous, free-flowing, water-soluble, granular solid constituting the enzyme reagent formulation.

11. A method as set forth in claim 10 wherein the nitrogen-containing polyoxyalkylene nonionic surfactant is solid and the polyoxypropylene chains thereof have an average molecular weight of less than about 4,000.

12. A method as set forth in claim 11 wherein the polyoxypropylene chains of the nitrogen-containing polyoxyalkylene nonionic surfactant have an average molecular weight of about 2,750 and the weight percentage of the polyoxyethylene units thereof is about 70%.

13. In a method of assaying a biological specimen for glucose utilizing a first liquid reagent containing o-dianisidine and a second liquid reagent containing glucose oxidase, peroxidase and buffering agents, the improvement which comprises preparing the first liquid reagent by dissolving in water a granular, water-soluble, substantially anhydrous, storage-stable reagent formulation containing o-dianisidine dihydrochloride and a nitrogen-containing polyoxyalkylene nonionic surfactant obtained by the sequential reaction of ethylenediamine with propylene oxide and ethylene oxide in the presence of a catalyst, the surfactant containing polyoxypropylene chains having an average molecular weight of between about 750 to about 6,750 and polyoxyethylene chains constituting between about 10 and about 80 weight percent of the surfactant and preparing the second liquid reagent by dissolving in water a second granular, water-soluble, substantially anhydrous, storage-stable reagent formulation containing glucose oxidase, peroxidase, gum arabic, mannitol, bovine serum albumin and the nitrogen-containing polyoxyalkylene nonionic surfactant and a third granular, water-soluble, substantially anhydrous, storage-stable reagent formulation containing a phosphate buffer component and the nitrogen-containing polyoxyalkylene nonionic surfactant.

14. A method as set forth in claim 13 wherein the polyoxypropylene chains of the nitrogen-containing polyoxyalkylene nonionic surfactant have an average molecular weight of about 2,750 and the weight percentage of the polyoxyethylene units thereof is about 70%.

* * * * *

UNITED STATES PATENT AND TRADEMARK OFFICE
CERTIFICATE OF CORRECTION

PATENT NO. : 3,953,295
DATED : April 27, 1976
INVENTOR(S) : Alexander A. Monte and Ching Chiang It is certified that error appears in the above-identified patent and that said Letters Patent are hereby corrected as shown below:

Col. 5, line 14, "loss" should read -- less --;

Col. 6, line 6, "through" should read -- thorough --;

Col. 6, line 21, "25" should read -- 25" --;

Col. 6, line 55, "certan" should read -- certain --;

Col. 8, line 7, "Dissolve" should read -- Dissolved --;

Col. 8, line 54, "formulations" should read -- formulation --.

In the Claims

Col. 11, line 44, "abou" should read -- about --;

Col. 11, line 45, "clam" should read -- claim --;

Col. 12, line 63, "to" should read -- and --.

Signed and Sealed this

Tenth Day of August 1976

[SEAL]

Attest:

RUTH C. MASON
Attesting Officer

C. MARSHALL DANN
Commissioner of Patents and Trademarks